US007288523B2

(12) United States Patent
Nordstedt et al.

(10) Patent No.: US 7,288,523 B2
(45) Date of Patent: Oct. 30, 2007

(54) PEPTIDE BINDING THE KLVFF-SEQUENCE OF AMYLOID-β

(75) Inventors: Christer Nordstedt, Mulhouse (FR); Jan Näslund, New York, NY (US); Johan Thyberg, Stockholm (SE); Lars O. Tjernberg, Spänga (SE); Lars Terenius, Uppsala (SE)

(73) Assignee: Neurochem (International) Limited, Ecublens (CH)

( * ) Notice: Subject to any disclaimer, the term of this patent is extended or adjusted under 35 U.S.C. 154(b) by 76 days.

(21) Appl. No.: 10/721,774

(22) Filed: Nov. 26, 2003

(65) Prior Publication Data

US 2004/0157781 A1    Aug. 12, 2004

Related U.S. Application Data

(60) Continuation of application No. 09/850,061, filed on May 8, 2001, now abandoned, which is a division of application No. 09/095,106, filed as application No. PCT/SE96/01621 on Dec. 9, 1996, now Pat. No. 6,331,440.

(60) Provisional application No. 60/009,386, filed on Dec. 29, 1995.

(30) Foreign Application Priority Data

Dec. 12, 1995    (SE)    .................... 9504467

(51) Int. Cl.
    *A61K 38/08*    (2006.01)
(52) U.S. Cl. .............................. 514/16; 514/17; 514/2; 530/328; 530/329
(58) Field of Classification Search ............... 514/2, 514/12, 14–17; 530/324, 326, 328, 329
    See application file for complete search history.

(56) References Cited

U.S. PATENT DOCUMENTS

| 4,116,768 A | 9/1978 | Isowa et al. |
|---|---|---|
| 5,002,872 A | 3/1991 | Gross |
| 5,470,951 A | 11/1995 | Roberts |
| 5,514,548 A | 5/1996 | Krebber et al. |
| 5,578,451 A | 11/1996 | Nishimoto |
| 5,593,846 A | 1/1997 | Schenk et al. |
| 5,652,334 A | 7/1997 | Roberts |
| 5,688,651 A | 11/1997 | Solomon |
| 5,721,130 A | 2/1998 | Seubert et al. |
| 5,753,624 A | 5/1998 | McMichael et al. |
| 5,780,587 A | 7/1998 | Potter |
| 5,817,626 A | 10/1998 | Findeis et al. |
| 5,837,672 A | 11/1998 | Schenk et al. |
| 5,851,996 A | 12/1998 | Kline |
| 5,854,204 A | 12/1998 | Findeis et al. |
| 5,854,215 A | 12/1998 | Findeis et al. |
| 5,869,093 A | 2/1999 | Weiner et al. |
| 5,891,991 A | 4/1999 | Wasco et al. |
| 5,985,242 A | 11/1999 | Findeis et al. |
| 6,022,859 A | 2/2000 | Kiessling et al. |
| 6,114,133 A | 9/2000 | Seubert et al. |

(Continued)

FOREIGN PATENT DOCUMENTS

| AU | 199870091 | 7/1998 |
|---|---|---|
| EP | 0584452 A1 | 3/1994 |
| EP | 0752886 B1 | 1/1998 |
| EP | 0584452 B1 | 7/2002 |
| WO | WO 94/05311 | 3/1994 |

(Continued)

OTHER PUBLICATIONS

Camilleri et al., "β-Cyclodextrin Interacts with the Alzheimer Amyloid β-A4 Peptide," FEBS Letters 341:256-258, 1994.
Fraser et al., "Effects of Sulfate Ions on Alzheimer β/A4 Peptide Assemblies: Implications for Amyloid Fibril-Proteoglycan Interactions," J. Neurochem. 59:1531-1540, 1992.
Lorenzo et al., "β-Amyloid Neurotoxicity Requires Fibril Formation and is Inhibited by Congo Red," Proc. Natl. Acad. Sci. USA 91:12243-12247, 1994.

(Continued)

*Primary Examiner*—Michael Borin
(74) *Attorney, Agent, or Firm*—Clark & Elbing LLP

(57) ABSTRACT

The invention relates to compounds of formula (I) or (II), which are of interest especially for inhibition of polymerization of amyloid β peptide, as model substances for synthesis of amyloid β peptide-ligands, as tools for the identification of other organic compounds with similar functional properties and/or as ligands for detection of amyloid deposits using e.g., positron emission tomography (PET). Formula (II) is: $R_1\text{-}A'\text{-}Y'\text{-}Leu\text{-}X'\text{-}Z'\text{-}B'\text{-}R_2$ in which X' means any group or amino acid imparting to the compound according to formula (I) the ability to bind to the KLVFF-sequence in amyloid β peptide, or two amino acids imparting the same ability, but with the proviso that one is not proline; Y' means any amino acid; Z' means any non-acidic amino acid; A' means a direct bond or an α-amino acid bonded at the carboxyl terminal of the α-carboxy group or a di-, tri-, tetra- or pentapeptide bonded at the carboxyl terminal of the α-carboxy group; B' means a direct bond or an α-amino acid bonded at the α-nitrogen or a di-, tri, tetra- or pentapeptide bonded at the α-nitrogen of the N-terminal α-amino acid; $R_1$ is H or —CO—$R_3$ bonded at the α-amino group of A'; $R_2$ is H, —$OR_4$ or $NR_5R_6$, all bonded to the α-carboxyl group of the α-carboxyterminal of B'; $R_3$ and $R_4$ are straight or branched carbon chain of 1-4 carbon atoms; $R_5$ and $R_6$ are independently H, alkyl, cycloalyl, aryl or substituted aryl or together are —$(CH_2)_n$— where n is 4-5; and $R_1$ and $R_2$ together can form a hydrocarbon ring or heterocyclic ring; all α-amino acids being either D- or L-isomers.

11 Claims, 6 Drawing Sheets

U.S. PATENT DOCUMENTS

| | | | |
|---|---|---|---|
| 6,261,569 | B1 | 7/2001 | Comis et al. |
| 6,277,826 | B1 | 8/2001 | Findeis et al. |
| 6,303,567 | B1 | 10/2001 | Findeis et al. |
| 6,319,498 | B1 | 11/2001 | Findeis et al. |
| 6,331,440 | B1 | 12/2001 | Nordstedt et al. |
| 6,436,903 | B1 | 8/2002 | Clayberger et al. |
| 6,610,658 | B1 | 8/2003 | Findeis et al. |
| 6,670,399 | B2 | 12/2003 | Green et al. |
| 6,689,752 | B2 | 2/2004 | Findeis et al. |
| 6,710,226 | B1 | 3/2004 | Schenk |
| 6,743,427 | B1 | 6/2004 | Schenk |
| 6,750,324 | B1 | 6/2004 | Schenk et al. |
| 6,761,888 | B1 | 7/2004 | Schenk et al. |
| 6,787,138 | B1 | 9/2004 | Schenk |
| 6,787,139 | B1 | 9/2004 | Schenk |
| 6,787,140 | B1 | 9/2004 | Schenk |
| 6,787,143 | B1 | 9/2004 | Schenk |
| 6,787,144 | B1 | 9/2004 | Schenk |
| 6,787,523 | B1 | 9/2004 | Schenk |
| 6,787,637 | B1 | 9/2004 | Schenk |
| 6,808,712 | B2 | 10/2004 | Schenk |
| 6,818,218 | B2 | 11/2004 | Schenk |
| 6,831,066 | B2 | 12/2004 | Findeis et al. |
| 6,866,849 | B2 | 3/2005 | Schenk |
| 6,866,850 | B2 | 3/2005 | Schenk |
| 6,875,434 | B1 | 4/2005 | Schenk |
| 7,060,670 | B1 | 6/2006 | Chalifour et al. |
| 2004/0157781 | A1 | 8/2004 | Nordstedt et al. |
| 2005/0090439 | A1 | 4/2005 | Chalifour et al. |
| 2006/0199771 | A1 | 9/2006 | Chalifour et al. |

FOREIGN PATENT DOCUMENTS

| | | |
|---|---|---|
| WO | WO 94/14836 | 7/1994 |
| WO | WO 94/19692 | 9/1994 |
| WO | WO 95/05393 | 2/1995 |
| WO | WO 95/05849 | 3/1995 |
| WO | WO 95/08999 | 4/1995 |
| WO | WO 95/12815 | 5/1995 |
| WO | WO 95/23166 | 8/1995 |
| WO | WO 95/31966 | 11/1995 |
| WO | WO 96/13583 | 5/1996 |
| WO | WO 96/28471 | 9/1996 |
| WO | WO 96/34887 | 11/1996 |
| WO | WO 96/37621 | 11/1996 |
| WO | WO 96/39834 | 12/1996 |
| WO | WO 97/08320 | 3/1997 |
| WO | WO 97/21728 | 6/1997 |
| WO | WO 97/32017 | 9/1997 |
| WO | WO 98/02462 | 1/1998 |
| WO | WO 98/05350 | 2/1998 |
| WO | WO 98/08868 | 3/1998 |
| WO | WO 98/22120 | 5/1998 |
| WO | WO 99/06587 | 2/1999 |
| WO | WO 99/27944 | 6/1999 |
| WO | WO 99/27949 | 6/1999 |
| WO | WO 99/58564 | 11/1999 |
| WO | WO 99/60021 | 11/1999 |
| WO | WO 99/60024 | 11/1999 |
| WO | WO 00/20027 | 4/2000 |
| WO | WO 00/26238 | 5/2000 |
| WO | WO 00/43039 | 7/2000 |
| WO | WO 00/52048 | 9/2000 |
| WO | WO 00/68263 | 11/2000 |
| WO | WO 00/72880 | 12/2000 |
| WO | WO 01/39796 | 6/2001 |

OTHER PUBLICATIONS

Wood et al., "Prolines and Amyloidogenicity in Fragments of the Alzheimer's Peptide β/A4," Biochem. 34:724-730, 1995.

Tjernberg et al., "Arrest of β-Amyloid Fibril Formation by a Pentapeptide Ligand", J. Biol. Chem., 1996, pp. 8545-8548, vol. 271, No. 15, The American Society for Biochemistry and Molecular Biology, Inc., Baltimore, Maryland, USA.

Findeis et al., "Modified-Peptide Inhibitors of Amyloid β-Peptide Polymerization," Biochem. 38:6791-6800, 1999.

Tjernberg et al., "Controlling Amyloid β-Peptide Fibril Formation with Protease-Stable Ligands," J. Biol. Chem. 272:12601-12605, 1997.

Alberts, "Molecular Biology of the Cell," Garland Publishing, p. 54, 1989.

Bard et al., "Peripherally Administered Antibodies Against Amyloid β-Peptide Enter the Central Nervous System and Reduce Pathology in a Mouse Model of Alzheimer Disease," Nature Med. 6(8):916-919, 2000.

Benkirane et al., "Antigenicity and Immunogenicity of Modified Synthetic Peotides Containing D-Amino Acid Residues," J. Biol. Chem. 268(35):26278-26285, 1993.

Chen et al., "Neurodegenerative Alzheimer-Like Pathology in PDAPP 717V->F Transgenic Mice," Prog. Brain Res. 117:327-334, 1998.

Cribbs et al., "All-D-Enantiomers of β-Amyloid Exhibit Similar Biological Properties to All-L-β-Amyloids, "J. Biol Chem. 272(11):7431-7436, 1997.

DeMattos et al., "Peripheral Anti-Aβ Antibody Alters CNS and Plasma Aβ Clearance and Decreases Brain Aβ Burden in a Mouse Model of Alzheimer's Disease, "Proc. Nat. Acad. Sci. U.S.A. 98(15):8850-8855, 2001.

Findels et al., "Modified-Peptide Inhibitors of Amyloid β-Peptide Polymerization, "Biochemistry 38(21):6791-6800, 1999.

Flood et al., "Topography of a Binding Site for Small Amnestic Peptides Deduced from Structure-Activity Studies: Relation to Amnestic Effect of Amyloid β Protein, "Proc. Nat. Acad. Sci. U.S.A. 91:380-384, 1994.

Frenkel, "Generation of Auto-Antibodies Towards Alzheimer's Disease Vaccination, "Vaccine 19(17-19):2615-2619, 2001.

Frenkel et al., "Immunization Against Alzheimer's β-Amyloid Plaques Cia EFRH Phage Administration, "Proc. Nat. Acad. Sci. U.S.A. 97(21):11455-11459, 2000.

Games et al., "Alzheimer-Type Neuropathology in Transgenic Mice overexpressing V717F =-Amyloid Precursor Protein, "Nature 373(6514):523-527, 1995.

Giullan et al., "The HHQK Domain of β-Amyloid Provides a Structural Basis for the Ummunopathology of Alzheimer's Disease, "J. Biol. Chem. 273(45):29719-29726, 1998.

Janus et al,. "Aβ Peptide Immunization Reduces Behavioral Impairment and Plaques in a Model of Alzheimer's Disease, "Nature 408(6815):979-982, 2000.

Jobling and Holmes, "Analysis of Structure and Function of the B Subunit of Cholera Toxin by the Use of Site-Directed Mutagenesis, "Mol. Microbiol. 5(7):1755-1767, 1991.

Kalaria, "The Blood-Brain Barrier and Cerebrovascular Pathology in Alzheimer's Disease, "Ann. N.Y. Acad. Sci. 893:113-125, 1999.

Lemere et al., Society for Neuroscience Abstracts, vol. 25, part 1, Abstract 519.6, 29th Annual Meeting Oct. 23-Oct. 28, 1999.

Morgan et al., "Aβ Peptide Vaccination Prevents Memory Loss in an Animal Model of Alzheimer's Disease, "Nature 408(6815):982-985, 2000.

Münch and Robinson, "Potential Neurotoxic Inflammatory Responses to Aβ Vaccination In Humans, "J. Neural Transmiss. 109(7-8):1081-1087, 2002.

Pike et al., "Neurodegeneration Induced by =-Amyloid Peptides in vitro: the Role of Peptide Assembly State, "J. Neurosci. 13(4) 1676-1687, 1993.

Schenk et al., "Immunization with Amyloid-β Attenuates Alzheimer-Disease-Like Pathology in the PDAPP Mouse, "Nature 400(6740):173-177, 1999.

Sela and Zisman, "Different Roles of D-Amino Acids In Immune Phenomena, "FASEB J. 11(6):449-456, 1997.

Skolnick and Fetrow, "From Genes to Protein Structure and Function: Novel Applications of Computational Approaches in the Genomic Era, "Trends Biotech. 18(1):37-39, 2000.

Soto et al., "Inhibition of Alzheimer's Amyloidosis by Peptides that Prevent β-Sheet Conformation, "*Biochem. Biophys. Res. Comm.* 226(3):672-680, 1996.

Thompson et al., "Vanadium Compounds as Insulin Mimics, "Chem. Rev. 99(19):2561-2571, 1999.

Tjernberg et al., "Controlling Amyloid β-Peptide Fibril Formation with Protease-Stable Ligands, "*J. Biol. Chem.* 272(19):12601-12605, 1997.

Tjernberg et al., "Controlling Amyloid β-Peptide Fibril Formation with Protease-Stable Ligands, "*J. Biol. Chem.* 272(28):17894, 1997.

Torneiro and Still, "Sequence-Selective Binding of Peptides in Water by a Synthetic Receptor Molecule, "*J. Am. Chem. Soc.* 117:5887-5888, 1995.

Van Regenmortel and Muller, "D-Peptides as Immunogens and Diagnostic Reagents, "*Curr. Opin. Biotech.* 9(4):377-382, 1998.

Wehner et al., "Cytoprotective Function of sAAPα In Human Keratinocytes, "*Eur. J. Cell. Biol.* 83(11-12):701-708, 2004.

Wong et al., "Absense of Pretease-Resistant Prion Protein in the Cerebrospinal Fluid of Creutzfeidt-Jakob Disease, "*J. Pathol.* 194(1):9-14, 2001.

Younkin, "Amyloid β Vaccination: Reduced Plaques and Improved Cognition, "*Nature Med.* 7(1):18-19, 2001.

International Search Report for PCT/CA00/00515 dated Dec. 5, 2000.

International Preliminary Report on Patentability from PCT/CA00/00515 dated Aug. 10, 2001.

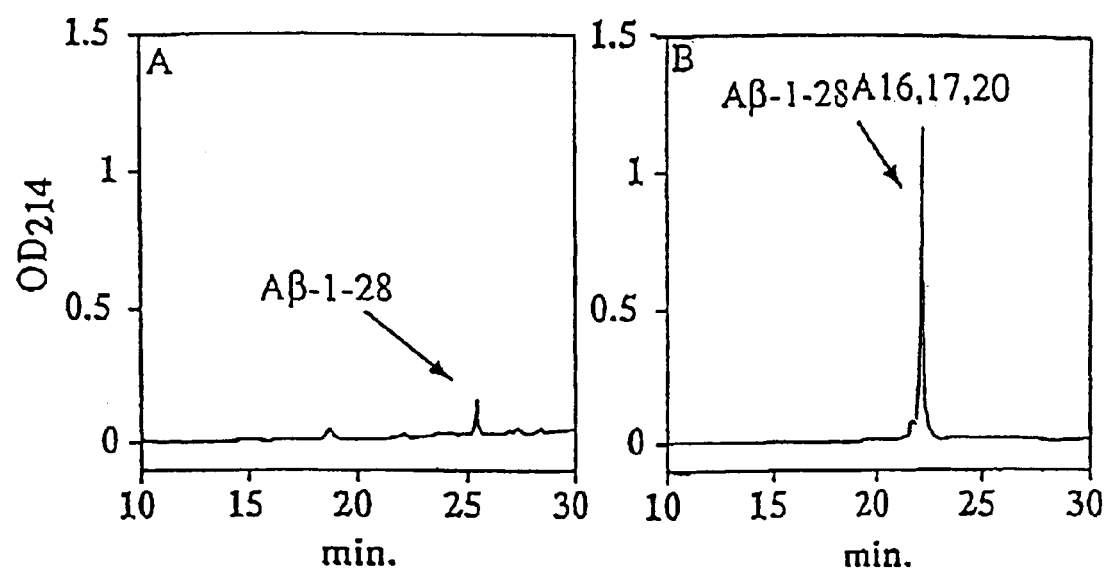
Fig. 3 A-B.

PEPTIDE BINDING THE KLVFF-SEQUENCE OF AMYLOID-β

CROSS REFERENCE TO RELATED APPLICATIONS

This application is a continuation of U.S. application Ser. No. 09/850,061, filed on May 8, 2001, now abandoned which is a divisional of U.S. application Ser. No. 09/095,106, filed on Jun. 10, 1998 now U.S. Pat. No. 6,331,440 which is a continuation of International Application No. PCT/SE96/01621, filed Dec. 9, 1996, which International Application was published by the International Bureau in English on Jun. 19, 1997, that designates the United States and which claims benefit of Swedish Application No. 9504467-3, filed Dec. 12, 1995, and U.S. Provisional Application No. 60/009,386, filed Dec. 29, 1995, which are herein incorporated by reference.

INTRODUCTION

The present invention relates to compounds, which are of special interest by their ability to bind to the KLVFF-sequence in the peptide amyloid β and to inhibit polymerization of the amyloid β peptide. The compounds according to the invention are e.g. useful as medicaments and as tools for identification of substances to be used in the treatment or prevention of amyloidosis.

BACKGROUND OF THE INVENTION

Amyloidosis is a condition which is characterized by the deposition of amyloid in organs or tissues of the human or animal body, either as a primary disease of unknown cause or secondary to chronic disease, such as tuberculosis or osteomyelitis. In addition, it has also been found that the pre-eminent neuropathological feature of Alzheimer's disease (AD), a chronic condition of brain atrophy, is the deposition of amyloid in the brain parenchyma and cerebrovasculature (D. J. Selkoe, *Neuron* 6, 487-498 (1991); D. J. Selkoe, *Annu. Rev. Cell Biol.* 10, 373-403 (1994)).

The basic component of such amyloid is a peptide termed amyloid β, or Aβ (G. C. Glenner, C. W. Wong, *Biochem, Biophys. Res. Commun.* 120, 885-890 (1984)). It is a 40 to 42 amino acids long proteolytic fragment of the Alzheimer amyloid precursor protein (APP), a protein expressed in most tissues (J. Kang, et al., *Nature* 325, 733-736 (1987)). Genetic and neuropathological studies provide strong evidence for a central role of Aβ in the pathogenesis of AD, but the pathophysiological consequences of the amyloid deposition are still unclear. However, it has been suggested that Aβ polymers and amyloid are toxic to neurons, either directly or indirectly, and hence cause neurodegeneration (C. Behl, J. B. Davis, R. Lesley, D. Schubert, *Cell* 77, 817-827 (1994); D. T. Loo, et al., ibid 90, 7951-7955 (1995)).

The amyloid associated with Alzheimer's disease (AD) consists of thin fibrils of polymerized Aβ. A rational pharmacological approach for the prevention of amyloidogenesis would therefore be to use drugs that specifically interfere with Aβ-Aβ interaction and polymerization. Previous studies showed that Aβ polymerization in vivo and in vitro is a highly specific process, which probably involves an interaction between binding sequences in the Aβ peptide (J. Näslund, et al., *Proc. Natl. Acad. Sci. USA* 91, 8378-8382 (1994); J. Näslund, et al., *Biochem. Biophys. Res. Commun.* 204, 790-787 (1994)).

Wood et al (S. J. Wood, R. Wetzel, J. D. Martin, M. R. Hurle, *Biochemistry* 34, 724-730 (1995)) suggest that amino acid residues within or close to Aβ-16-20 are important for the adoption of the correct β-pleated sheet structure of Aβ and show that amino acids 17-23 in the amyloid β peptide (Aβ) are essential for fibril formation and probably make up the β-sheet core of the fibrils. In addition, Wood et al. have investigated the ability of their peptides to form amyloid fibrils in a solution containing solely the mutated or the wild-type peptide. However, no method or principle which makes it possible to inhibit Aβ of wild type from forming amyloid fibrils is devised and no use of the peptides as medicaments is suggested.

WO 95/08999 relates to amelioration of amnesia in Alzheimer's disease caused by deposition of amyloid β protein. Three peptides are disclosed, which overcome the amnestic effects of β-12-28, a peptide homologous to Aβ. In addition, WO 95/08999 describes the screening of several other peptides, which were neither significantly amnestic nor memory enhancing, of which one is KLVFF, SEQ. NO. 15 of the sequence listing therein.

In EP 0 584 452, novel amyloid precursor proteins and the sequences thereof are disclosed. Peptide sequences that comprise KLVFF are revealed, However, neither binding to amyloid β peptide nor any inhibition of the polymerization thereof is suggested.

SUMMARY OF THE INVENTION

Thus, the polymerization of the amyloid β peptide (Aβ) into amyloid fibrils is a critical step in the pathogenesis of Alzheimer's disease.

In vitro and in vivo studies of Aβ have shown that the Aβ molecules interact with a high degree of specificity during polymerization and fibril formation. It was assumed that ligands which bind to recognition sequences would be capable of inhibiting Aβ polymerization and possibly also dissolve preformed Aβ polymers in situ. The strategy in finding such Aβ ligands was to identify critical binding regions in Aβ and, based on their sequences, develop a compound capable of blocking the Aβ-Aβ binding.

According to the invention, it was hypothesized that compounds capable of binding to regions in the Aβ-molecule critical for its polymerization might inhibit amyloid fibril formation, as described in more detail below.

According to the invention, it has now been found that the Lys-Leu-Val-Phe-Phe (KLVFF) sequence [SEQ ID NO.: 1] in Aβ is necessary for polymerization to occur. Peptides incorporating this sequence bind to Aβ and are capable of blocking the fibril formation of Aβ-1-40 and are therefore potentially useful as drugs.

In addition, compounds have been found, which
1) are capable of binding to full-length Aβ,
2) are capable of blocking Aβ fibril formation and
3) do not form fibrils by themselves.

In addition, it has also been found that alanine-substituted Aβ-1-28 (Ala at position 16, 17, 20), in contrast to wild-type Aβ-1-28, does not form fibrils.

Thus, it was concluded that the Lys-Leu-Val-Phe-Phe (16-20) motif serves as a structural basis for the development of peptide and non-peptide agents aimed at inhibiting amyloidogenesis in-vivo. This is a novel finding and the compounds are of utmost interest as being useful as drugs for Alzheimer's disease.

Further, the findings according to the invention are even more surprising on the basis of what was concluded from WO 95/08999 mentioned above. In WO 95/08999, it was concluded that KLVFF is not a potential candidate for the development of substances that can antagonize binding of Aβ and thus attenuate symptoms and progression of AD. Even though the teaching of said WO publication indicates the opposite, according to the present invention, it has now been found that KLVFF on the contrary is most useful for the development of new compounds defined by Formula (I) and (II) below.

DETAILED DESCRIPTION OF THE INVENTION

The present invention relates to compounds which are able to bind to the Lys-Leu-Val-Phe-Phe-sequence, or KLVFF-sequence, in the peptide amyloid β. More specifically, the compounds according to the invention are defined by their formula (I):

R$_1$-A'-Y'-Leu-X'-Z'-B'—R$_2$  (I)

in which

X' means any group or amino acid imparting to the compound of formula (I) the ability to bind to the KLVFF-sequence in amyloid β peptide, or two amino acids imparting the same ability, but with the proviso that one is not proline;

Y' means any amino acids

Z' means any non-acidic amino acid:

A' means a direct bond or an α-amino acid bonded at the carboxyl terminal of the α-carboxy group or a di-, tri-, tetra- or pentapeptide bonded at the carboxyl terminal of the α-carboxy group;

B' means a direct bond or an α-amino acid bonded at the α-nitrogen or a di-, tri-, tetra- or pentapeptide bonded at the α-nitrogen of the N-terminal α-amino acid;

R$_1$ is H or —CO—R$_3$ bonded at the α-amino group of A';

R$_2$ is H, —OR$_4$ or NR$_5$R$_6$ all bonded to the α-carboxyl group of the α-carboxyterminal of B';

R$_3$ is a straight or branched carbon chain of 1-4 carbon atoms;

R$_4$ is a straight or branched carbon chain of 1-4 carbon atoms;

R$_5$ and R$_6$ independently are H, alkyl, cycloalkyl, aryl or substituted aryl or together are —(CH$_2$)$_n$—, where n is 4-5;

R$_1$ and R$_2$ together can form a hydrocarbon ring or heterocyclic ring; and all the α-amino acids can be either D- or L-isomers;

with the proviso that (I) is not Lys-Leu-Val-Phe-Phe.

With alkyl is preferably meant a chain of 4 or less carbon atoms, e.g. methyl, ethyl, propyl or butyl.

With cykloalkyl is preferably meant a ring of 3, 4, 5 or 6 carbon atoms.

Aryl preferably means a phenyl group, which can be substituted, preferably by a methyl, ethyl, propyl or butyl group, an amino or a methoxy, ethoxy, propoxy or butoxy group.

In a preferred embodiment of the present invention, the compound exhibits an ability to inhibit polymerization of amyloid β peptide.

In one embodiment of the invention, all the amino acids of the compound are D-isomers.

In one embodiment of the invention, Y' is Lys, and in a particular embodiment of the invention, Z' is Phe, resulting in a compound of the following formula:

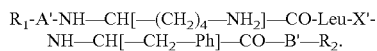

R$_1$-A'-NH—CH[—(CH$_2$)$_4$—NH$_2$]—CO-Leu-X'-NH—CH[—CH$_2$—Ph]-CO—B'—R$_2$.

In an alternative embodiment of the invention, Y' is Phe.

Preferred are compounds, wherein X' is Val-Val.

In one embodiment of the present aspect of the invention, R$_1$ is acetyl.

In an alternative embodiment of the invention, R$_1$ is H. According to another embodiment, R$_2$ is H. Alternatively, R$_1$ and R$_2$ are both H.

A second aspect of the present invention is the use of a compound of formula:

R$_1$-A'-Y'-Leu-X'-Z'-B'—R$_2$  (II)

in which

X' means any group or amino acid imparting to the compound of formula (II) the ability to bind to the KLVFF-sequence in amyloid β peptide, or two amino acids imparting the same ability, but with the proviso that one is not proline;

Y' means any amino acid;

Z' means any non-acidic amino acid;

A' means a direct bond or an α-amino acid bonded at the carboxyl terminal of the α-carboxy group or a di-, tri-, tetra- or pentapeptide bonded at the carboxyl terminal of the α-carboxy group;

B' means a direct bond or an α-amino acid bonded at the α-nitrogen or a di-, tri-, tetra- or pentapeptide bonded at the α-nitrogen of the N-terminal α-amino acid;

R$_1$ is H or —CO—R$_3$ bonded at the β-amino group of A';

R$_2$ is H, —OR$_4$ or NR$_5$R$_6$ all bonded to the α-carboxylgroup of the α-carboxyterminal of B';

R$_3$ is a straight or branched carbon chain of 0.1-4 carbon, atoms;

R$_4$ is a straight or branched carbon chain of 1-4 carbon atoms;

R$_5$ and R$_6$ independently are H, alkyl, cycloalkyl, aryl or substituted aryl or together are —(CH$_2$)$_n$— where n is 4-5;

R$_1$ and R$_2$ can together form a hydrocarbon ring or heterocyclic ring; and all the α-amino acids can be either D- or L-isomers;

for inhibition of polymerization of amyloid β peptide, as a model substance for synthesis of amyloid β peptide-ligands for inhibition of polymerization of amyloid β peptide, as a tool for the identification of other organic compounds with similar functional properties or as ligand for detection of amyloid deposits using e.g. positron emission tomography (PET).

With alkyl is preferably meant a chain of 4 or less carbon atoms, e.g. methyl, ethyl, propyl or butyl.

With cykloalkyl is preferably meant a ring of 3, 4, 5 or 6 carbon atoms.

Aryl preferably means a phenyl group, which can be substituted, preferably by a methyl, ethyl, propyl or butyl group, an amino or a methoxy, ethoxy, propoxy or butoxy group.

In one embodiment of this second aspect of the invention, a compound is used, wherein all the amino acids are D-isomers.

In a particular embodiment of this aspect of the invention, Y' is Lys. A particular embodiment is when Z' is Phe, resulting in a compound of the following formula:

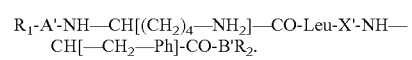

R$_1$-A'-NH—CH[(CH$_2$)$_4$—NH$_2$]—CO-Leu-X'-NH—CH[—CH$_2$—Ph]-CO-B'R$_2$.

In an alternative embodiment, a compound is used, wherein Y' is Phe while Z' is any non-acidic amino acid.

In a preferred embodiment of this aspect of the invention, a compound is used, wherein X' is Val-Val.

In one embodiment of the use according to the invention, $R_1$ is acetyl. Alternatively, $R_1$ and/or $R_2$ are H.

Yet another aspect of the present invention is a compound according to the invention for use as a medicament.

Also claimed is the use of a compound, preferably of the formula (I) or (I), which is able to bind to the KLVFF-sequence in amyloid β peptide and which has the ability to inhibit polymerization of amyloid β peptide, for the manufacture of a medicament for the treatment or prevention of amyloidosis, especially in the treatment or prevention of Alzheimer's disease associated with amyloidosis, for the treatment or prevention of demens in patients with Down's syndrome, for the treatment or prevention of hereditary cerebral hemorrhage with amyloidosis (Dutch type) or for the prevention of fibril formation of human amyloid protein.

Further, a last aspect of the present invention is a composition comprising a compound according to formula II and optionally a ligand capable of binding or interacting with the compound according to formula II and a carrier.

Said composition can e.g. be adapted for injection in a liquid carrier or for oral administration in a tablet or capsule.

Carriers are known for persons skilled in the art.

For clarification the following definitions are given:
K is lysine (Lys), L is leucine (Leu), V is valine (Val), F is phenylalanine (Phe), A is alanine (Ala) and E is glutamic acid (Glu).

As used herein, "any group giving the compound according to formula (I) the ability to bind to the KLVFF-sequence in the amyloid β peptide" means that this group gives the compound a structure, which can fulfill the requirements given in claim 1.

The hydrocarbon ring or heterocyclic ring has preferably 4-6 atoms, preferably C, N and S.

DESCRIPTION OF THE FIGURES

FIGS. 3A and B. Content of non-aggregated peptide in the supernatants from incubations of wild-type and Ala-substituted Aβ-1-28 as analyzed by HPLC.

EXPERIMENTAL

EXAMPLE 1 a) Ten-mers corresponding to consecutive sequences of Aβ-1-40 were synthesized on a filter matrix using the SPOT-technique (the peptides were synthesized essentially as described by Frank [R. Frank, *Tetrahedron* 42, 9217-9232 (1992)]. Briefly, a spacer corresponding to 2 molecules of β-alanine was coupled to cellulose membranes (Whatman lChr). The peptides were synthesized on these derivatized membranes using Fmoc protected and pentafluorophenyl-activated amino acids (AMS Biotechnology) dissolved in N-methylpyrrolidone. Coupling efficiency was monitored using bromphenol blue.). We synthesized the thirty-one possible 10-mers of the Aβ-1-40. Peptide no. 1 corresponds to amino acids 1-10, peptide no. 2 to amino acids 2-11 etc. The filter-bound peptides were incubated with radioactive Aβ-1-40. Following washing of the filter in high-salt buffer, bound radioactivity was estimated by autoradiography and densitometry. Following blocking with 0.05% Tween-20 in Tris-buffered saline (TBS), the filter was incubated in the presence of 20 μM $^{125}$I-labelled Aβ-1-40 at 20° C. for 12 h in TBS, pH 7.3, supplemented with 1% bovine serum albumin. The filter was then washed repeatedly in the same buffer containing 0.5 M NaCl and dried. Radioactivity bound to the filter was visualized by autoradiography and quantitated using a densitometer.

b) Peptide no. 11 (EVHHQKLVFF) and indicated N- and C-terminal truncated fragments were synthesized using the same technique as described above and analyzed for affinity to $^{125}$I-labelled Aβ-1-40.

c) Sensorgram from BIAcore 2000. Aβ-1-40, at three different concentrations in running buffer, pH 7.4. Aβ-1-40 was injected during 10 minutes over a sensor-chip derivatized with the peptide KLVFF-βA-βA-C.

d) Each amino acid residue in KLVFF was systematically replaced with A and analyzed for affinity to $^{125}$I-labelled Aβ-1-40. Non-specific interactions have been compensated for by subtracting the signal from a surface derivatized with C alone.

Figure 1:
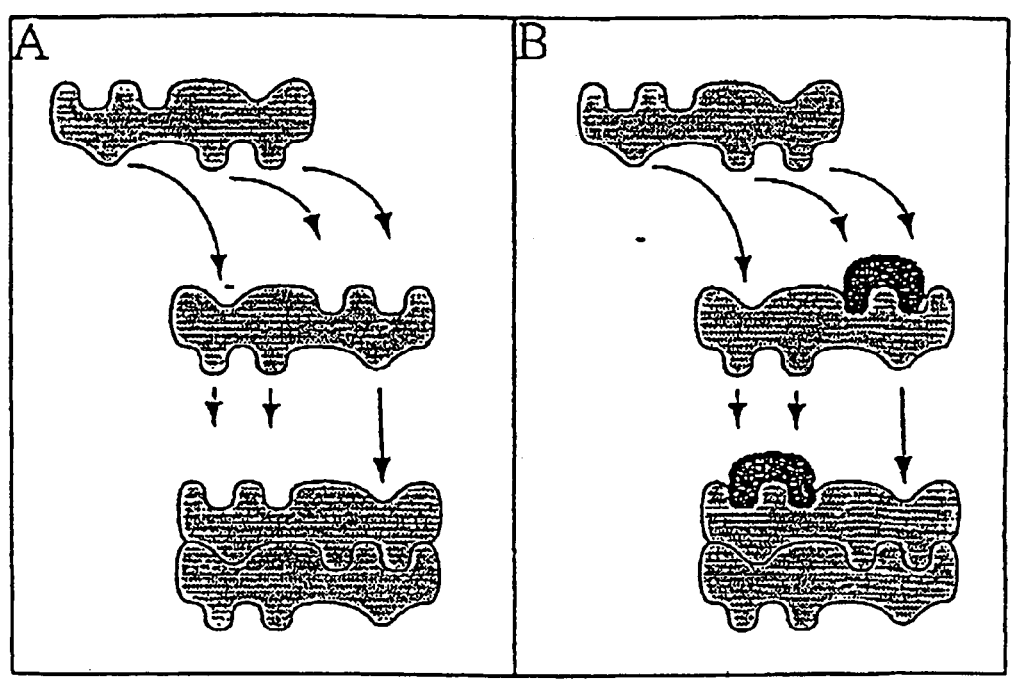
FIGS. 1A and B. Aβ-amyloid polymerization.
Figure 2:
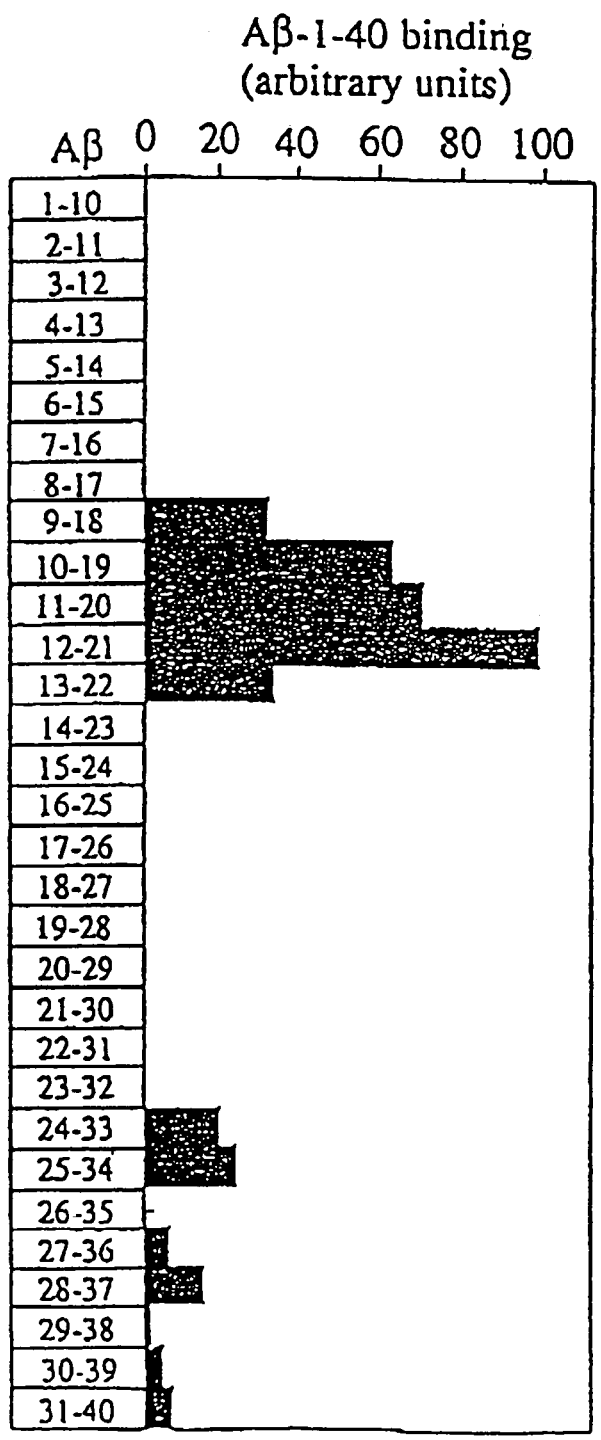
FIG. 2A. Ten-mers corresponding to consecutive sequences of Aβ-1-40. Radioactivity bound to the filter was detected by autoradiography and quantified by densitometry.
FIG. 2B. [SEQ ID NOS.: 1, 2 and 5-38] EVHHQKLVFF and N and C-terminal truncated fragments were synthesized and analyzed for affinity to $^{125}$I-labeled Aβ-1-40.
FIG. 2C. [SEQ ID NOS.: 39-43] Each amino acid residue in KLVFF was systematically replaced with Ala and analyzed for affinity to $^{125}$I-labeled Aβ-1-40.
FIG. 2D. [SEQ ID NO.: 44] Sensorgram from surface plasmon resonance spectroscopy (BIAcore 2000).
Figure 2:
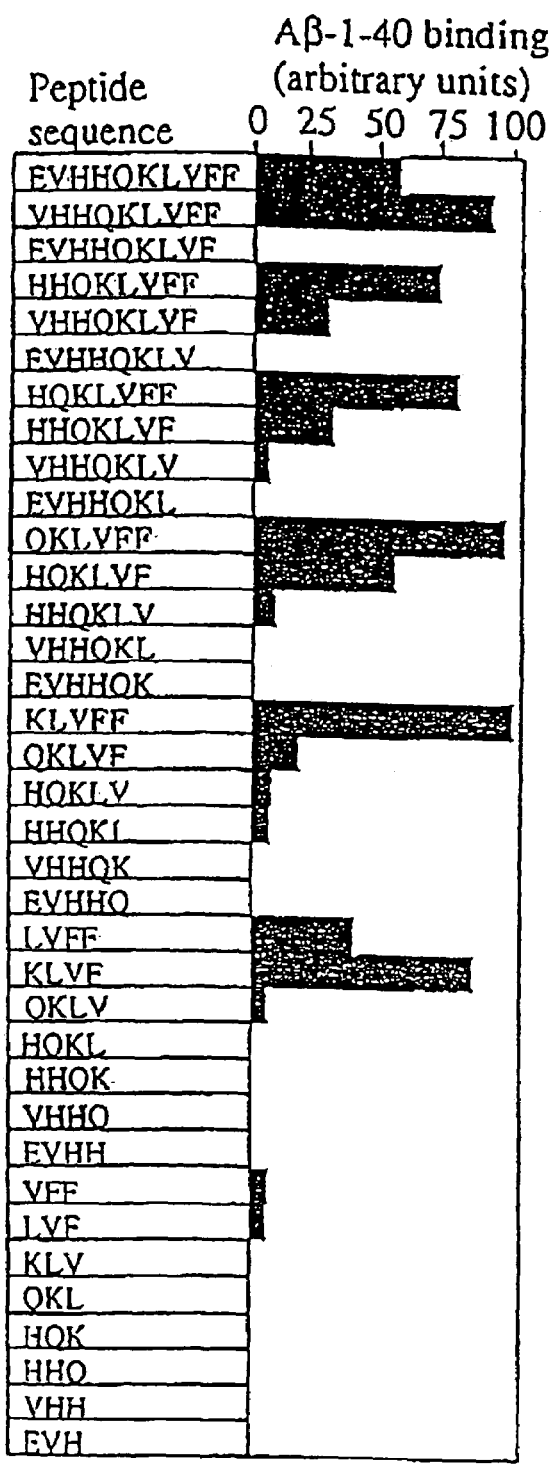
Figure 2:
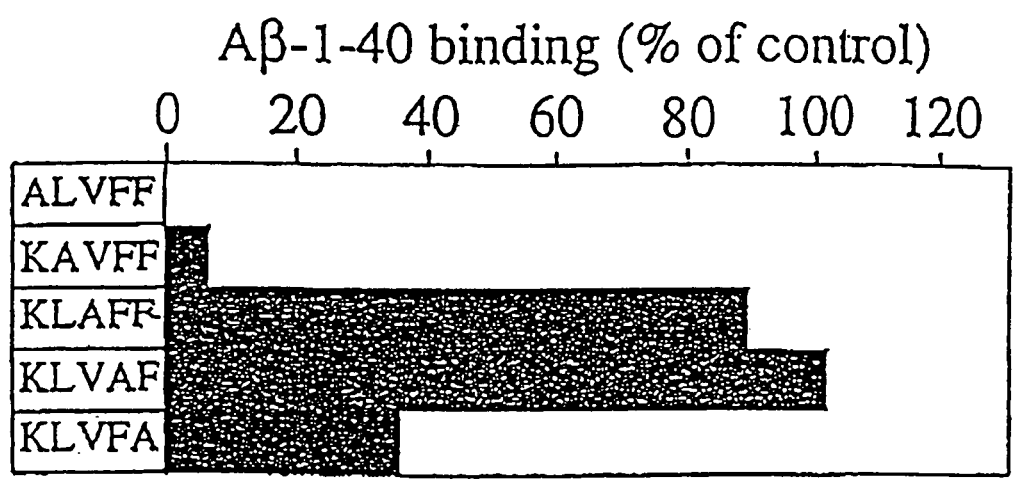
Figure 2:
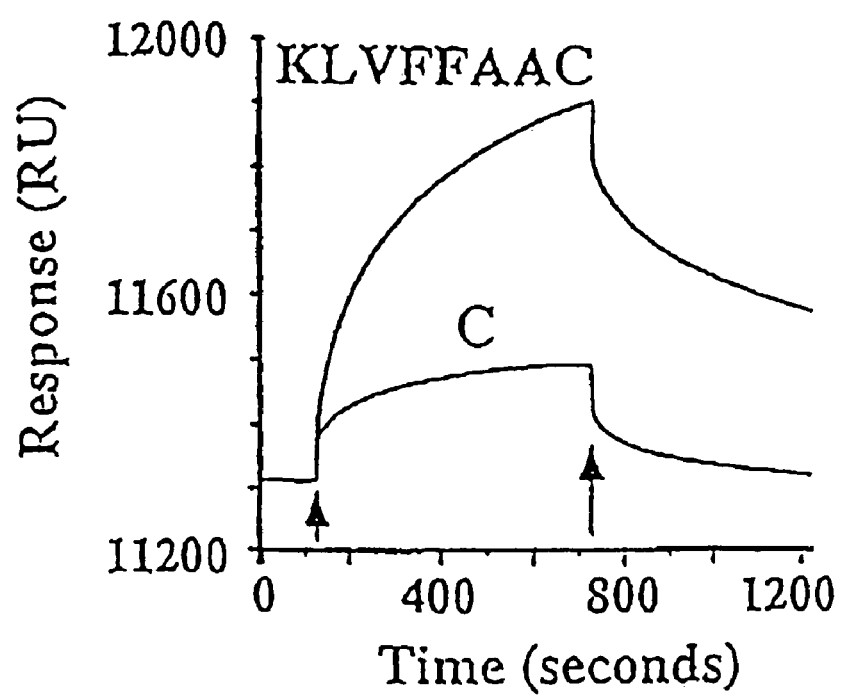

Results a) The measured binding should be interpreted as semi-quantative, since the coupling efficiency and therefore tha amount of peptide per spot may vary. A region located in the central part of Aβ (Aβ-9-18 to Aβ-13-22) displayed prominent binding of radioactive Aβ-1-40. Another binding region was the hydrophobic C-terminus of the molecule (D. Burdick, et al, *J. Biol. Chem.* 267, 546-554 (1992)) but binding here was considerably weaker (FIG. 2A).

b) Being located in the centre of the binding region, peptide no. 11 (corresponding to Aβ-11-20) was selected for further studies. This peptide, as well as N- and C-terminal-fragments thereof, were synthesized using the same technique as described previously. The shortest peptide still displaying high Aβ binding capacity had the sequence KLVFF, corresponding to amino acids 16-20 of Aβ (FIG. 2B). By systematically substituting the amino acid residues in the KLVFF sequence with alanine, we found that the first, second and fifth residues (i.e. KLXXF) were critical for binding (FIG. 2C).

c) The interaction between soluble Aβ-1-40 and immobilized KLVFF was monitored in real-time (FIG. 2D) using surface plasmon resonance spectroscopy (BIAcore, Pharmacia) (BIAcore 2000 (Pharmacia Biosensor AB, Sweden) was used for real-time studies based on surface plasmon resonance spectroscopy. The peptide was immobilized using thiol coupling. The running buffer consisted of 10 mM HEPES, 0.15 M NaCl, 3.4 mM EDTA and 0.05% surfactant P20 as described. [U. Jansson, M. Malmqvist, *Adv. Biosens.* 2, 291-336 (1992)]). The binding was not saturable, indicating that Aβ-1-40 bound to immobilized KLVFF could interact with other Aβ-1-40 molecules in a polymerization reaction.

d) AA served as linker between the active peptide and the chip (upper trace) and cysteine alone, indicating non-specific binding, (C) as control (lower trace). Arrows indicate start and stop of injection (FIG. 2D).

EXAMPLE 2

To investigate if the KLXXF [SEQ ID NO.: 3] motif was required for Aβ polymerization, we synthesized Aβ-1-28, a well-studied Aβ fragment that readily forms amyloid fibrils (D.A. Kirschner, et al., *Proc. Nati. Acad. Sci. USA* 84, 6953-6957 (1987); C.J. Barrow, M.G. Zagorski, *Science* 253, 179-82 (1997); C. Nordstedt, et al., *J. Biol. Chem.* 269, 30773-30776 (1994))) and mutated Aβ-1-28 where the KLVFF sequence was substituted with AAVFA [SEQ ID NO. 4] (Aβ-1-28$^{AAVFA}$).

Aβ-1-28 (FIG. 3A) and AP-1-28$^{AAVFA}$ (FIG. 3B) were incubated at 200 µM in TBS for 24 h at 37° C. in a shaking water bath. After incubation, the tubes were centrifuged at 20,000 g for 20 min and the content of non-aggregated peptide in the supernatants (FIG. 3A, B) was analyzed using an established C4 RPLC system (12) whereas the aggregated peptides in the pellets were analyzed by electron microscopy after adsorption to formvar-coated grids and negative staining with 2% uranyl acetate in water.

Results

Following incubation at a concentration of 200 µM for 24 h at 37° C., Aβ-1-28 aggregated (FIG. 3A) and formed large fibril bundles, whereas Aβ-1-28$^{AAVFA}$ almost completely failed to aggregate (FIG. 3B) and only formed a few dispersed fibrils.

EXAMPLE 3

Aβ-1-40 was incubated at 100 µM in TBS for 48 h at 37° C. in a shaking water bath, either alone or together with 100 µM AcKLVFFNH$_2$. The polymerized material was adsorbed to formvar-coated grids and negatively stained with 2% uranyl acetate in water.

Results

Incubation of synthetic Aβ-1-40 at 100 µM for 48 h at 37° C. in a physiological buffer led to polymerization and formation of amyloid fibrils arranged in parallel in densely packed bundles, as previously shown (C. Nordstedt, et al., *J. Biol. Chem.* 269, 30773-30776 (1994)). When Aβ-1-40 was coincubated with AcQKLVFFNH$_2$ at equimolar concentrations, this type of fibrils did not form. Instead, only a few occasional fibrils embedded in a diffuse background of small rod-like aggregates, similar to those formed by AcQKLVT-FNH$_2$ itself, could be detected.

EXAMPLE 4

The peptides were synthesized essentially as described by Frank (Frank R, 1992, Tetrahedron 42:9217-9232). Briefly, a spacer corresponding to 2 molecules of β-alanine was coupled to cellulose membranes (Whatman XX). The peptides were synthesized on these derivatized membranes using Fmoc protected and pentafluorophenyl-activated amino acids (AMS biotechnology) dissolved in N-methylpyrrolidone. Coupling efficiency was monitored using bromphenol blue.

Results

The KLXXF motif in the Aβ molecule is not only critical for polymerization and fibril-formation. During non-amyloidogenic processing of APP, the molecule is cleaved between amino acid residues $K^{16}$ and $L^{17}$ (F. S. Esch, et al., *Science* 248, 1122-1124 (1990)), leading to the formation of a fragment of Aβ termed p3 and corresponding to Aβ-17-40 or Aβ-17-42 (C. Haass, A. Y. Hung, M. G. Schlossmacher, D. B. Teplow, D. J. Selkoc, *J. Biol. Chem.* 260, 3021-3024 (1993)). Through this metabolic pathway the present binding sequence is disrupted. This may explain why p3 is not capable of forming amyloid in vitro or in vivo (J. Näslund, et al., *Proc. Natl. Acad. Sci. USA* 91, 8378-8382 (1994); J. Näslund, et al., *Biochem. Biophys. Res. Commun.* 204, 780-787 (1994)). The KLXXF motif is highly sequence specific. The most apparent example of this is the finding that substitution of a single amino acid leads to virtually complete loss of Aβ binding capacity.

EXAMPLE 5

In an additional series of experiments, it was demonstrated that KLVFF binds stereo specifically to the homologous sequence in Aβ (i.e. Aβ-16-20). By screening combinatorial pentapeptide libraries exclusively composed of D-amino acids (lowercase) with labelled KLVFF, several ligands with a motif containing phenylalanine (f) in the second and leucine (l) in the third position were identified (e.g. lflrr). By using a short peptide in the screening, known to bind to a region in Aβ critical for its polymerization (i.e. KLVFF), the risk of identifying D-pentapeptides that interact with nonrelevant regions in Aβ (N- or C-terminal to Aβ-16-20) was eliminated. Like KLVFF, the D-amino acid ligands were found not only to bind to Aβ but also to inhibit amyloid fibril formation. Since peptides built up of D-amino acids are resistant to proteolytic degradation, these ligands may be beneficial for inhibition of amyloidogenesis in vivo. The results further indicate that KLVFF will be useful in the identification of small organic molecules (e.g. by screening of substance libraries) with the ability to bind to Aβ in this relevant region and inhibit amyloid fibril formation (candidate drugs for the treatment of Alzheimer disease and other related amyloidoses).

Discussion and Conclusion

Previous studies of putative inhibitors of amyloid fibril formation showed that cyclodextrins (P. Camilleri, N. J. Haskind, D. R. Howlett, *FEBS Lett.* 341, 256-258 (1994)) and Congo red (A. Lorenzo, S. Yankner, *Proc. Natl. Acad. Sci. USA* 91, 12243-12247. (1994)) may have such properties. The usefulness of these molecules as lead or model substances in development of anti-Alzheimer amyloid drugs is, however, compromised by their relative lack of specificity. Cyclodextrins have primarily been used to increase the solubility of a wide range of lipophilic drugs and it is unlikely that they would display any specificity for Aβ in vivo. Congo red, which is used in histochemistry to detect amyloid, binds to a wide array of non-Aβ amyloids as well as to other proteins with a high content of β-pleated sheet structures (W. G. Turnell, J. T. Finch, *J. Mol. Biol.* 227, 1205-1223 (1992)).

Due to the extreme insolubility of amyloid, strong chaotropic agents or potent organic solvents are required for its dissolution (C. L. Masters, et al., *Proc. Natl. Acad. Sci. USA* 82, 4245-4249 (1985)), the concept of dissolving amyloid deposits in situ under physiological conditions may seem futile. However, the bulk of the individual molecules in amyloid are probably not joined by covalent bonds and the deposition of Aβ into amyloid is, at least at some stages, a dynamic and reversible process (J. E. Maggio, et al., *ibid.,*

89, 5462-5466 (1992)). Hence, a molecule capable of binding to a site in the Aβ molecule that is critical for fibril formation with an affinity higher than native Aβ should have reasonable chances to inhibit amyloid growth and maybe also specifically dissolve amyloid fibrils.

In conclusion, we have identified an Aβ sequence, KLVFF, which is required for amyloid fibril formation. The KLVFF peptide may serve as a model substance for the synthesis of non-peptide Aβ-ligands, that interfere with the polymerization of Aβ molecules.

Previous studies suggested that amino acid residues within or close to Aβ-16-20 are important for the adoption of the correct β-pleated sheet structure of Aβ (18) and the proteolytic processing of its precursor (14).

We have now shown that this region harbors at least one binding sequence required for the polymerization of Aβ into amyloid fibrils. It was also demonstrated that short peptides incorporating Aβ-16-20 can function as ligands that bind to Aβ and inhibit the formation of amyloid fibrils. Since these peptide ligands are relatively small, they are amenable for identification of other organic molecules with similar functional properties. Non-peptide homologues of KLVFF should be useful as pharmacological drugs for the treatment, of Alzheimer's disease in the future.

We claim:

1. A method for inhibiting Aβ fibril formation in a patient in need thereof, comprising administering to said patient a therapeutic effective amount of a compound defined by the Formula:

$$R_1\text{-AA-}R_2$$

wherein AA in said Formula corresponds to an amino acid sequence selected from the group consisting of:
His-Gln-Lys-Leu-Val-Phe;
His-His-Gln-Lys-Leu-Val-Phe-Phe-Ala-Glu;
His-His-Gln-Lys-Leu-Val-Phe;
Val-His-His-Gln-Lys-Leu-Val-Phe-Phe-Ala;
Val-His-His-Gln-Lys-Leu-Val-Phe;
Tyr-Glu-Val-His-His-Gln-Lys-Leu-Val-Phe; and
Gly-Tyr-Glu-Val-His-His-Gln-Lys-Leu-Val;
and wherein
$R_1$ is H or —CO—$R_3$ bonded at the α-amino group of the N-terminal of AA;
$R_2$ is H or —O$R_4$ or N$R_5R_6$ all bound to the α-carboxyl group of the α-carboxyterminal of AA;
$R_3$ is a straight or branched carbon chain of 1-4 carbon atoms;
$R_4$ is a straight or branched carbon chain of 1-4 carbon atoms;
$R_5$ and $R_6$ independently are H, alkyl, cycloalkyl, aryl or substituted aryl or together are -(CH$_2$)$_n$-, where n is 4-5;
$R_1$ and $R_2$ together can form a hydrocarbon ring or heterocyclic ring; and
said amino acids can be either D- or L-isomers.

2. A method for inhibiting Aβ fibril formation, comprising contacting an amyloid β containing environment with a polymerization inhibiting effective amount of a compound defined by the Formula:

$$R_1\text{-AA-}R_2$$

wherein AA in said Formula corresponds to an amino acid sequence selected from the group consisting of:
His-Gln-Lys-Leu-Val-Phe;
His-His-Gln-Lys-Leu-Val-Phe-Phe-Ala-Glu
His-His-Gin-Lys-Leu-Val-Phe;
Val-His-His-Gln-Lys-Leu-Val-Phe-Phe-Ala;
Val-His-His-Gln-Lys-Leu-Val-Phe;
Tyr-Glu-Val-His-His-Gln-Lys-Leu-Val-Phe; and
Gly-Tyr-Glu-Val-His-His-Gln-Lys-Leu-Val;
and wherein
$R_1$ is H or —CO—$R_3$ bonded at the α-amino group of the N-terminal of AA;
$R_2$ is H or —O$R_4$ or N$R_5R_6$ all bound to the α-carboxyl group of the α-carboxyterminal of AA;
$R_3$ is a straight or branched carbon chain of 1-4 carbon atoms;
$R_4$ is a straight or branched carbon chain of 1-4 carbon atoms;
$R_5$ and $R_6$ independently are H, alkyl, cycloalkyl, aryl or substituted aryl or together are -(CH$_2$)$_n$-, where n is 4-5;
$R_1$ and $R_2$ together can form a hydrocarbon ring or heterocyclic ring; and
said amino acids can be either D- or L-isomers.

3. The method of claim 1 or 2, wherein all the amino acids of said amino acid sequence are D-isomers.

4. The method of claim 1 or 2, wherein $R_1$ is acetyl.

5. The method of claim 1 or 2, wherein $R_1$ is H or $R_2$ is H.

6. The method of claim 1, wherein the patient has Alzheimer's disease or another disease characterized by amyloidosis.

7. A method for inhibiting Aβ fibril formation in a patient in need thereof, comprising administering to said patient a therapeutic effective amount of a peptide consisting of an amino acid sequence selected from the group consisting of:
His-Gln-Lys-Leu-Val-Phe;
His-His-Gln-Lys-Leu-Val-Phe-Phe-Ala-Glu;
His-His-Gln-Lys-Leu-Val-Phe;
Val-His-His-Gln-Lys-Leu-Val-Phe-Phe-Ala;
Val-His-His-Gln-Lys-Leu-Val-Phe;
Tyr-Glu-Val-His-His-Gln-Lys-Leu-Val-Phe; and
Gly-Tyr-Glu-Val-His-His-Gln-Lys-Leu-Val.

8. The method of claim 7, wherein said amino acid sequence comprises amino acids in the D-configuration.

9. The method of claim 8, wherein all of said amino acids are amino acids in the D-configuration.

10. The method of claim 7, wherein said peptide is conjugated to a carrier.

11. The method of claim 7, wherein the patient has Alzheimer's disease or another disease characterized by amyloidosis.

* * * * *

UNITED STATES PATENT AND TRADEMARK OFFICE
CERTIFICATE OF CORRECTION

| | | |
|---|---|---|
| PATENT NO. | : 7,288,523 B2 | Page 1 of 1 |
| APPLICATION NO. | : 10/721774 | |
| DATED | : October 30, 2007 | |
| INVENTOR(S) | : Christer Nordstedt et al. | |

It is certified that error appears in the above-identified patent and that said Letters Patent is hereby corrected as shown below:

On the title page, under item (56), page 2, in References Cited, in OTHER PUBLICATIONS,
    in Findels et al., replace "Findels" with --Findeis--.
    in Frenkel et al., replace "Cia" with --Via--.
    in Games et al., replace "=" with --β--.
    in Pike et al., replace "=" with --β--.
    in Skolnick and Fetrow, replace "37" with --34--.

On the title page, under item (56), page 3, in References Cited, in OTHER PUBLICATIONS,
    in Wong et al., replace "Pretease" with --Protease--; and
    in Wong et al., replace "Creutzfeidt" with --Creutsfeldt--.

Column 3, Line 26, replace "acids" with --acid--.

Column 4, Line 31, replace "0.1-4" with --1.4--.

Column 6, Line 32, replace "tha" with --the--.

Column 7, Line 45, replace "AcQKLVT-" with --AcQKLVF- --.

Column 8,
    Line 1, replace "260" with --268--.
    Line 45, replace "S. Yankner" with --B. Yankner--.

Signed and Sealed this

Twenty-eighth Day of October, 2008

JON W. DUDAS
*Director of the United States Patent and Trademark Office*

SEQUENCE LISTING

```
<160> NUMBER OF SEQ ID NOS: 44

<210> SEQ ID NO 1
<211> LENGTH: 5
<212> TYPE: PRT
<213> ORGANISM: Amyloidosis

<400> SEQUENCE: 1

Lys Leu Val Phe Phe
 1               5

<210> SEQ ID NO 2
<211> LENGTH: 10
<212> TYPE: PRT
<213> ORGANISM: Amyloidosis

<400> SEQUENCE: 2

Glu Val His His Gln Lys Leu Val Phe Phe
 1               5                   10

<210> SEQ ID NO 3
<211> LENGTH: 5
<212> TYPE: PRT
<213> ORGANISM: Amyloidosis
<220> FEATURE:
<221> NAME/KEY: PEPTIDE
<222> LOCATION: (3)..(4)
<223> OTHER INFORMATION: Amino acids 3 and 4 are Xaa wherein Xaa =
      any amino acid.

<400> SEQUENCE: 3

Lys Leu Xaa Xaa Phe
 1               5

<210> SEQ ID NO 4
<211> LENGTH: 5
<212> TYPE: PRT
<213> ORGANISM: Amyloidosis

<400> SEQUENCE: 4

Ala Ala Val Phe Ala
 1               5

<210> SEQ ID NO 5
<211> LENGTH: 6
<212> TYPE: PRT
<213> ORGANISM: Amyloidosis

<400> SEQUENCE: 5

Gln Lys Leu Val Phe Phe
 1               5
```

<210> SEQ ID NO 6
<211> LENGTH: 9
<212> TYPE: PRT
<213> ORGANISM: Amyloidosis

<400> SEQUENCE: 6

Val His His Gln Lys Leu Val Phe Phe
 1               5

<210> SEQ ID NO 7
<211> LENGTH: 9
<212> TYPE: PRT
<213> ORGANISM: Amyloidosis

<400> SEQUENCE: 7

Glu Val His His Gln Lys Leu Val Phe
 1               5

<210> SEQ ID NO 8
<211> LENGTH: 8
<212> TYPE: PRT
<213> ORGANISM: Amyloidosis

<400> SEQUENCE: 8

His His Gln Lys Leu Val Phe Phe
 1               5

<210> SEQ ID NO 9
<211> LENGTH: 8
<212> TYPE: PRT
<213> ORGANISM: Amyloidosis

<400> SEQUENCE: 9

Val His His Gln Lys Leu Val Phe
 1               5

<210> SEQ ID NO 10
<211> LENGTH: 8
<212> TYPE: PRT
<213> ORGANISM: Amyloidosis

<400> SEQUENCE: 10

Glu Val His His Gln Lys Leu Val
 1               5

<210> SEQ ID NO 11
<211> LENGTH: 7
<212> TYPE: PRT
<213> ORGANISM: Amyloidosis

<400> SEQUENCE: 11

His Gln Lys Leu Val Phe Phe
 1               5

<210> SEQ ID NO 12
<211> LENGTH: 7
<212> TYPE: PRT
<213> ORGANISM: Amyloidosis

<400> SEQUENCE: 12

His His Gln Lys Leu Val Phe
 1               5

<210> SEQ ID NO 13
<211> LENGTH: 7

```
<212> TYPE: PRT
<213> ORGANISM: Amyloidosis

<400> SEQUENCE: 13

Val His His Gln Lys Leu Val
 1               5

<210> SEQ ID NO 14
<211> LENGTH: 7
<212> TYPE: PRT
<213> ORGANISM: Amyloidosis

<400> SEQUENCE: 14

Glu Val His His Gln Lys Leu
 1               5

<210> SEQ ID NO 15
<211> LENGTH: 6
<212> TYPE: PRT
<213> ORGANISM: Amyloidosis

<400> SEQUENCE: 15

His Gln Lys Leu Val Phe
 1               5

<210> SEQ ID NO 16
<211> LENGTH: 6
<212> TYPE: PRT
<213> ORGANISM: Amyloidosis

<400> SEQUENCE: 16

His His Gln Lys Leu Val
 1               5

<210> SEQ ID NO 17
<211> LENGTH: 6
<212> TYPE: PRT
<213> ORGANISM: Amyloidosis

<400> SEQUENCE: 17

Val His His Gln Lys Leu
 1               5

<210> SEQ ID NO 18
<211> LENGTH: 6
<212> TYPE: PRT
<213> ORGANISM: Amyloidosis

<400> SEQUENCE: 18

Glu Val His His Gln Lys
 1               5

<210> SEQ ID NO 19
<211> LENGTH: 5
<212> TYPE: PRT
<213> ORGANISM: Amyloidosis

<400> SEQUENCE: 19

Gln Lys Leu Val Phe
 1               5

<210> SEQ ID NO 20
<211> LENGTH: 5
<212> TYPE: PRT
<213> ORGANISM: Amyloidosis
```

```
<400> SEQUENCE: 20

His Gln Lys Leu Val
 1               5

<210> SEQ ID NO 21
<211> LENGTH: 5
<212> TYPE: PRT
<213> ORGANISM: Amyloidosis

<400> SEQUENCE: 21

His His Gln Lys Leu
 1               5

<210> SEQ ID NO 22
<211> LENGTH: 5
<212> TYPE: PRT
<213> ORGANISM: Amyloidosis

<400> SEQUENCE: 22

Val His His Gln Lys
 1               5

<210> SEQ ID NO 23
<211> LENGTH: 5
<212> TYPE: PRT
<213> ORGANISM: Amyloidosis

<400> SEQUENCE: 23

Glu Val His His Gln
 1               5

<210> SEQ ID NO 24
<211> LENGTH: 4
<212> TYPE: PRT
<213> ORGANISM: Amyloidosis

<400> SEQUENCE: 24

Leu Val Phe Phe
 1

<210> SEQ ID NO 25
<211> LENGTH: 4
<212> TYPE: PRT
<213> ORGANISM: Amyloidosis

<400> SEQUENCE: 25

Lys Leu Val Phe
 1

<210> SEQ ID NO 26
<211> LENGTH: 4
<212> TYPE: PRT
<213> ORGANISM: Amyloidosis

<400> SEQUENCE: 26

Gln Lys Leu Val
 1

<210> SEQ ID NO 27
<211> LENGTH: 4
<212> TYPE: PRT
<213> ORGANISM: Amyloidosis
```

```
<400> SEQUENCE: 27

His Gln Lys Leu
 1

<210> SEQ ID NO 28
<211> LENGTH: 4
<212> TYPE: PRT
<213> ORGANISM: Amyloidosis

<400> SEQUENCE: 28

His His Gln Lys
 1

<210> SEQ ID NO 29
<211> LENGTH: 4
<212> TYPE: PRT
<213> ORGANISM: Amyloidosis

<400> SEQUENCE: 29

Val His His Gln
 1

<210> SEQ ID NO 30
<211> LENGTH: 4
<212> TYPE: PRT
<213> ORGANISM: Amyloidosis

<400> SEQUENCE: 30

Glu Val His His
 1

<210> SEQ ID NO 31
<211> LENGTH: 3
<212> TYPE: PRT
<213> ORGANISM: Amyloidosis

<400> SEQUENCE: 31

Val Phe Phe
 1

<210> SEQ ID NO 32
<211> LENGTH: 3
<212> TYPE: PRT
<213> ORGANISM: Amyloidosis

<400> SEQUENCE: 32

Leu Val Phe
 1

<210> SEQ ID NO 33
<211> LENGTH: 3
<212> TYPE: PRT
<213> ORGANISM: Amyloidosis

<400> SEQUENCE: 33

Lys Leu Val
 1

<210> SEQ ID NO 34
<211> LENGTH: 3
<212> TYPE: PRT
<213> ORGANISM: Amyloidosis
```

-continued

```
<400> SEQUENCE: 34

Gln Lys Leu
  1

<210> SEQ ID NO 35
<211> LENGTH: 3
<212> TYPE: PRT
<213> ORGANISM: Amyloidosis

<400> SEQUENCE: 35

His Gln Lys
  1

<210> SEQ ID NO 36
<211> LENGTH: 3
<212> TYPE: PRT
<213> ORGANISM: Amyloidosis

<400> SEQUENCE: 36

His His Gln
  1

<210> SEQ ID NO 37
<211> LENGTH: 3
<212> TYPE: PRT
<213> ORGANISM: Amyloidosis

<400> SEQUENCE: 37

Val His His
  1

<210> SEQ ID NO 38
<211> LENGTH: 3
<212> TYPE: PRT
<213> ORGANISM: Amyloidosis

<400> SEQUENCE: 38

Glu Val His
  1

<210> SEQ ID NO 39
<211> LENGTH: 5
<212> TYPE: PRT
<213> ORGANISM: Amyloidosis

<400> SEQUENCE: 39

Ala Leu Val Phe Phe
  1               5

<210> SEQ ID NO 40
<211> LENGTH: 5
<212> TYPE: PRT
<213> ORGANISM: Amyloidosis

<400> SEQUENCE: 40

Lys Ala Val Phe Phe
  1               5

<210> SEQ ID NO 41
<211> LENGTH: 5
<212> TYPE: PRT
<213> ORGANISM: Amyloidosis
```

```
<400> SEQUENCE: 41

Lys Leu Ala Phe Phe
 1               5

<210> SEQ ID NO 42
<211> LENGTH: 5
<212> TYPE: PRT
<213> ORGANISM: Amyloidosis

<400> SEQUENCE: 42

Lys Leu Val Ala Phe
 1               5

<210> SEQ ID NO 43
<211> LENGTH: 5
<212> TYPE: PRT
<213> ORGANISM: Amyloidosis

<400> SEQUENCE: 43

Lys Leu Val Phe Ala
 1               5

<210> SEQ ID NO 44
<211> LENGTH: 8
<212> TYPE: PRT
<213> ORGANISM: Amyloidosis

<400> SEQUENCE: 44

Lys Leu Val Phe Phe Ala Ala Cys
 1               5
```